United States Patent [19]

Kessels

[11] Patent Number: 5,504,250
[45] Date of Patent: Apr. 2, 1996

[54] PROCESS FOR THE PREPARATION OF D-(−)-PHENYLGLYCINE CHLORIDE HYDROCHLORIDE

[75] Inventor: Raoul Kessels, Barcelona, Spain

[73] Assignee: Westpur Investments Limited, Isle of Man, United Kingdom

[21] Appl. No.: 202,816

[22] Filed: Feb. 28, 1994

[30] Foreign Application Priority Data

Mar. 9, 1993 [NL] Netherlands ............................ 9300422

[51] Int. Cl.$^6$ .................................................. C07C 51/58
[52] U.S. Cl. ........................................................ 562/863
[58] Field of Search ............................................... 562/863

[56] References Cited

FOREIGN PATENT DOCUMENTS 264689  8/1989  Germany .

*Primary Examiner*—Paul J. Killos
*Attorney, Agent, or Firm*—Kane, Dalsimer, Sullivan, Kurucz, Levy, Eisele and Richard

[57] ABSTRACT

The invention relates to a process for the preparation of D-(−)-phenylglycine chloride hydrochloride by chlorinating D-(−)-phenylglycine hydrochloride, which as such is prepared in situ from D-(−)-phenylglycine and hydrochloric acid gas, in a solvent. According to the invention chlorination of the hydrochloride is carried out in a non-chlorinated solvent or a mixture of non-chlorinated solvents in the presence of a reaction promoting medium.

Chlorination is carried out through the addition of $PCl_5$, but preferably the $PCl_5$ is prepared in situ from $PCl_3$ and $Cl_2$ gas.

17 Claims, 1 Drawing Sheet

PROCESS FOR THE PREPARATION OF D-(-)-PHENYLGLYCINE CHLORIDE HYDROCHLORIDE

BACKGROUND OF THE INVENTION

1. Field of the Invention

The invention relates to a process for the preparation of D-(-)-phenylglycine chloride hydrochloride by chlorinating D-(-)-phenylglycine hydrochloride, which as such is prepared in situ from D-(-)-phenylglycine and hydrochloric acid gas, in a solvent.

2. Brief Description of Related Art

D-(-)-phenylglycine chloride hydrochloride is a particularly valuable substance; after all, this substance is used in the preparation of antibiotics. D-(-)-phenylglycine chloride hydrochloride is an indispensable starting material in the preparation of the half-synthetic penicillins, such as ampicillin; the half-synthetic cephalosporin, cefalhexin; and bactericides such as tetrazolylpenams and spiropenams.

As is known, D-(-)-phenylglycine chloride hydrochloride is prepared by chlorinating D-(-)-phenylglycine hydrochloride with phosphorus pentachloride in a solvent which does not dissolve the starting product and the end product and whereby phosphorus oxychloride is obtained as a by-product. Separation by filtration yields a non-dividable mixture of D-(-)-phenylglycine chloride hydrochloride and the non-reacted starting substance. As D-(-)-phenylglycine chloride hydrochloride is used in the preparation of medicines, it must be of the highest possible purity. Nowadays it is a requirement that the content of D-(-)-phenylglycine chloride hydrochloride in the end-product is 96% or more.

In order to meet this requirement it is necessary in the known methods to carry out the chlorination in chlorinated solvents such as: dichloromethane, chloroform, dichloroethane, carbon tetrachloride or mixtures of such chlorinated solvents. It is generally known that this type of chlorinated solvents is very harmful. For humans they are toxic and some of them are even carcinogenic. For the environment they are very harmful because they are not biologically degradable. These adverse characteristics cause various problems when using the above-mentioned chlorinated solvents in the preparation of D-(-)-phenylglycine chloride hydrochloride. From a hygienic and safety point of view the treatment of the process solution is obstructed. The losses during the working up of the process solution have a destructive effect on the environment, and the volatility of these solvents aggravates the problem even more. There are also disadvantages with a view to the end-product, as there is always a small but not removable amount of solvent remaining in the dried D-(-)-phenylglycine chloride hydrochloride. As this product is used in the preparation of medicines it is not acceptable that it should contain toxic or carcinogenic substances. In addition it must be considered that legislation in western countries, and gradually also in the rest of the world, is focussed at a decrease and eventual discontinuation of the use of chlorinated solvents.

All the patents and technical literature known up to now describe the use of chlorinated solvents for the preparation of D-(-)-phenylglycine chloride hydrochloride. The French patent specification 1.332.557 (Jul. 19, 1963) [Chem. Abstr. 60 P1761b] to Bristol-Meyers, Co., describes the preparation in both dichloromethane and carbon tetrachloride. In the article by G. A. Hardcastle et al (J. Org. Chem., 31 (1966), 897–899) the preparation of D-(-)-phenylglycine chloride hydrochloride is also carried out in dichloromethane. In 1973 Ajinomoto Co., Inc. patented the preparation of the same product in JP 73 13.301 (Feb. 20, 1973) [Chem. Abstr. 78 P13-6660h] using dichloroethane as solvent. Chinoin in HU 183.548 (Aug. 29, 1983) [Chem. Abstr. 100 P68733e] describes the process using dichloromethane or carbon tetrachloride as solvent. The latest known patent is from 1989, DD 264,689 (Feb. 8, 1989) [Chem. Abstr. 111 P97719n], in which VEB Berlin-Chemie patents the preparation of D-(-)-phenylglycine chloride hydrochloride in dichloromethane.

The use of non-chlorinated solvents in the preparation of D-(-)-phenylglycine chloride hydrochloride has not been possible up to now. Chlorination of D-(-)-phenylglycine hydrochloride carried out in a non-chlorinated solvent yields an end-product having such a low content of the desired compound, that it is not suitable for the manufacture of medicines. That means that the use of non-chlorinated solvents is excluded as one obtains D-(-)-phenylglycine chloride hydrochloride of poor quality, due to the starting substance being left behind in the end-product.

Moreover, it should be noted that the product obtained does not show a well defined crystalline structure, but that there are substantial differences in particle size and also, that these have, in part, an amorphous structure. This is disadvantageous when using this D-(-)-phenylglycine chloride hydrochloride in the preparation of medicines as these reactions are also carried out heterogeneously and the reaction rates of the different modifications and sizes vary.

The invention provides thus a process in which the above-mentioned disadvantages are alleviated.

SUMMARY OF THE INVENTION

To this end the invention provides a process for the preparation of D-(-)-phenylglycine chloride hydrochloride by chlorinating D-(-)-phenylglycine hydrochloride, which as such is prepared in situ from D-(-)-phenylglycine and hydrochloric acid gas, in a solvent, characterized in that chlorination of the hydrochloride is carried out in a non-chlorinated solvent or a mixture of non-chlorinated solvents in the presence of a reaction promoting medium. This yields an end product containing from 99–100% D-(-)-phenylglycine chloride hydrochloride and a substance with a true crystalline structure.

Surprisingly it has been shown that, if the chlorination is carried out in a non-chlorinated solvent, to which an amount of reaction promoting medium, viz. an oxychloride or an acylchloride ismadded, then inexplicably, D-(-)-phenylglycine chloride hydrochloride of very good quality, that is to say in crystalline form, is obtained, with a content of up to 100%.

Surprisingly it has also been shown, that the product obtained by the process according to the invention crystallizes out as fine needles, well-defined and uniform in size (see FIG. 1), which is in contrast to the product obtained by using chlorinated solvents, whereby no true crystallization takes place, but rather an amorphous substance is obtained (FIG. 2). The end-product is not uniform and has different structures. The advantage of using a uniformly crystalline product in the preparation of antibiotics is that the crystals formed here have the same reactivity, therefore allowing the process to be carried out more effectively.

DETAILED DESCRIPTION OF THE PREFERRED EMBODIMENTS OF THE INVENTION

The chlorination according to the invention occurs normally through the addition of $PCl_5$. Preferably the $PCl_5$ is prepared in situ from $PCl_3$ and $Cl_2$ gas. The $PCl_5$ formed in this way is more freely available for the chlorination reaction than when $PCl_5$ directly, occurring in solid form, is added.

The non-chlorinated solvent normally used according to the invention is cyclohexane, cumene, ethyl benzene, heptane, mesitilene, pentane, toluene, xylene, etc. or a mixture thereof, while preferably p-xylene is used. A particular advantage of these solvents is that they are biologically degradable, and therefore not harmful for the environment.

If the reaction promoting medium used is an oxychloride, then one applies as a rule phosphorus oxychloride, thionyl chloride, sulfuryl chloride or vanadyl chloride, while if acyl chloride is used, then one applies generally acetyl chloride, propionyl chloride or benzoyl chloride.

According to the process of the invention, 5–45% by weight of the reaction promoting medium, viz the oxychloride or acyl chloride is added to a suspension of 5–30% by weight of D-(-)-phenylglycine hydrochloride in a non-chlorinated biologically degradable solvent or mixture of solvents at a temperature of 10°–40° C., followed by the addition of the chlorinating medium and stirring of the mixture for 2–15 hours at 10°–40° C., after which the crystalline D-(-)-phenylglycine chloride hydrochloride thus formed is separated by, for instance filtration, and the reaction promoting medium and the solvent are recovered from the filtrate for reuse. The filtrate can be divided into its components by, for instance fractionated distillation, and the recovered oxychloride or acylchloride and solvent can be reused in a following reaction.

The process according to the invention is preferably carried out thus, that to a suspension of 7–12% by weight of hydrochloride, 20–25% by weight of the reaction promoting medium is added in a non-chlorinated solvent at 20°–25° C., followed by the addition of the chlorination medium and stirring the mixture for 5–10 hours at 20°–25° C.

It should be noted, that the solvents coming into consideration are those which are biologically degradable and which are, moreover, not reactive with respect to phosphorus pentachloride, oxychlorides, acylchlorides and hydrochloric acid. The above-mentioned solvents meet those requirements.

The invention further comprises an antibiotic, prepared in a manner known as such, using the D-(-)-phenylglycine chloride hydrochloride prepared according to the present invention.

DESCRIPTION OF THE DRAWINGS

The D-(-)-phenylglycine chloride hydrochloride obtained according to the invention using p-xylene and phosphorus oxychloride, is represented in FIG. 1 of the drawing. It clearly shows that the product formed is a finely crystalline one consisting of needles.

Figure 1:
Figure 2:
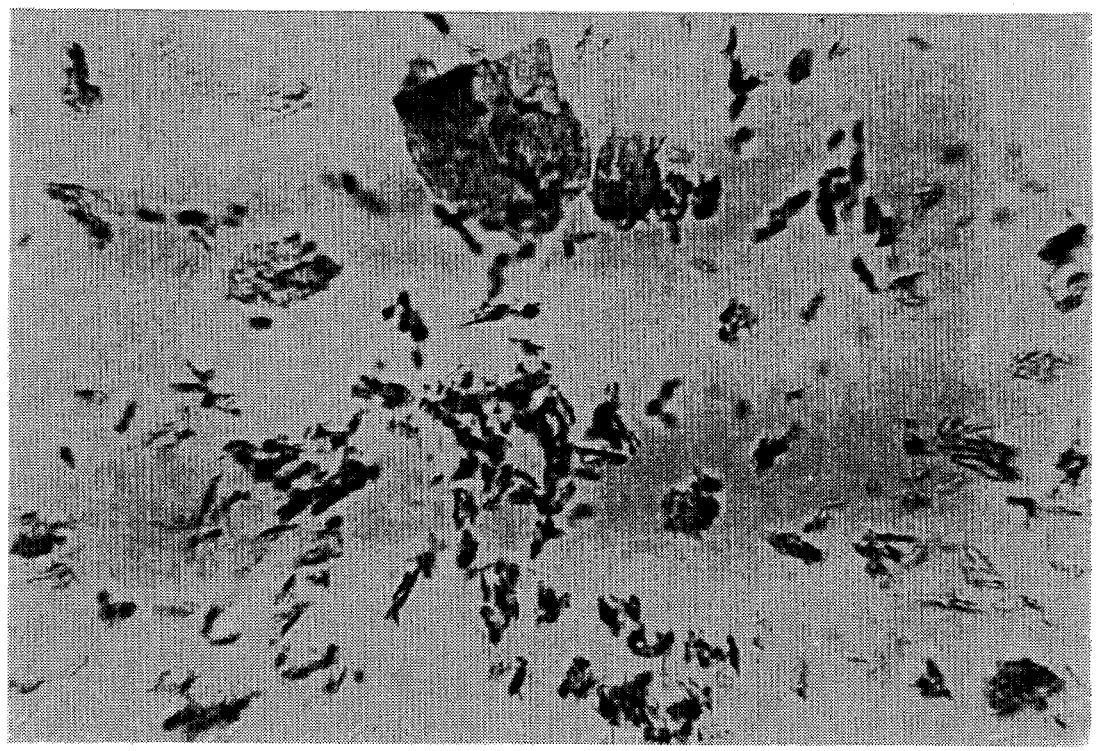
FIG. 2 of the drawing shows a product prepared according to the known method in dichloromethane, a chlorinated solvent. The thus prepared D-(-)-phenylglycine chloride hydrochloride is in part amorphous, implying an irregular crystalline structure.

The invention will now be further elucidated by means of the following, non-limitative examples.

EXAMPLE I 90 ml of toluene and 10 g (0.066 mol) of D-(-)-phenylglycine were brought into a 250 ml flask and stirred. Dry hydrochloric acid gas was led in for one hour at 25° C. to convert the D-(-)-phenylglycine into its hydrochloride. De D-(-)-phenylglycine hydrochloride suspension obtained was cooled to 23° C. adding 30.2 g of phosphorus oxychloride. While stirring, a solution of 16.57 g (0.080 mol) phosphorus pentachloride was dosed into 80 ml of toluene for 45 min. The mixture was stirred for a further 10 hours at 23° C. and then filtered and the crystals obtained were washed with 30 ml of toluene. After drying once under vacuum 13.32 g of a white crystalline substance was obtained.

The content was determined by means of potentiometric anhydrous titration. The end-product was dissolved in methanol and titrated with a solution of NaOH in methanol. By this procedure the amount of D-(-)-phenylglycine chloride hydrochloride and D-(-)-phenylglycine hydrochloride in the end-product can be measured, as in methanol different pKs correspond with the different acids.

The content of D-(-)-phenylglycine chloride hydrochloride was 99.1% and of D-(-)-phenylglycine hydrochloride 0.9%.

EXAMPLE II 80 ml of Cyclohexane and 11 g (0.073 mol) of D-(-)-phenylglycine were brought into a 250 ml flask and the mixture was stirred. Dry hydrochloric acid gas was led in for one hour at 25° C. to convert the D-(-)-phenylglycine into its hydrochloride. The D-(-)-phenylglycine hydrochloride suspension obtained was retained at 25° C. and 12.5 g of acetyl chloride and 12 g (0.087 mol) of phosphorus trichloride were added. 6,2 g (0.087 mol) of chlorine was dosed for 2 hours under cooling, after which the mixture was again stirred for 7 hours at 25° C. The suspension obtained was filtered and the crystals obtained were washed with 30 ml of cyclohexane. After drying under vacuum 14.77 g of a white crystalline substance was obtained.

The content was measured potentiographically as in Example I and amounted to 98.7% D-(-)-phenylglycine chloride hydrochloride and 1.3% D-(-)-phenylglycine hydrochloride.

EXAMPLE III 160 ml of p-xylene and 11 g (0.073 mol) of D-(-)-phenylglycine were brought into a 250 ml flask and the mixture was stirred. Dry hydrochloric acid gas was led in for one hour at 25° C. to convert the D-(-)-phenylglycine into its hydrochloride. The D-(-)-phenylglycine hydrochloride suspension obtained was cooled to 23° C. and 36.8 g of phosphorus oxychloride and 18.2 g (0.087 mol) of phosphorus pentachloride were added. The mixture was again stirred for 9 hours at 23° C., filtered and the crystals obtained were washed with 30 ml of p-xylene. After drying under vacuum 14.74 g of a white crystalline substance was obtained.

The content was determined potentiographically as in Example I and amounted to 99.5% D-(-)-phenylglycine chloride hydrochloride and 0.5% D-(-)-phenylglycine hydrochloride.

The filtrate together with the wash solution were brought into a flask provided with a fractionating column and a cooler. The mixture was heated, and four fractions were distilled off. The composition of the fractions was determined by means of gas chromatography.

| Fraction | Boiling range (°C.) | Amount | Composition |
|---|---|---|---|
| a | 100–110 | 20 ml | POCl$_3$ |
| b | 110–125 | 8 ml | 97% POCl$_3$ |
| c | 125–135 | 18 ml | 95% p-xylene |
| d | 135–145 | 170 ml | p-xylene |

EXAMPLE IV 80 ml of p-xylene from fraction d of the distillation of Example III and 11 g (0.073 mol) of D-(-)-phenylglycine were brought into a 250 ml flask and the mixture was stirred. Dry hydrochloric acid gas was added for one hour at 25° C. to convert the D-(-)-phenylglycine into its hydrochloride. The D-(-)-phenylglycine hydrochloride suspension obtained was cooled to 23° C. and fraction b from Example III and 13 ml of phosphorus oxychloride from fraction a of Example III were added. 18.2 g (0.087 mol) of phosphorus pentachloride dissolved in 80 ml of p-xylene from fraction d of Example III was dosed for 45 min. The mixture was again stirred for 5 hours at 23° C., filtered and the crystals obtained washed with 30 ml of p-xylene. After drying under vacuum 14.69 g of a white crystalline substance was obtained.

The content was determined potentiographically as in Example I and amounted to 99.8% D-(-)-phenylglycine chloride hydrochloride and 0.2% D-(-)-phenylglycine hydrochloride.

EXAMPLE V 80 ml of ethylbenzene and 11 g (0.073 mol) of D-(-)-phenylglycine were brought into a 250 ml flask and the mixture was stirred. Dry hydrochloric acidgas was added for one hour at 25° C. to convert the D-(-)-phenylglycine into its hydrochloride. The D-(-)-phenylglycine hydrochloride suspension obtained was cooled to 23° C. and 24.3 g of sulfuryl chloride and 12 g (0.087 mol) of phosphorus trichloride were added. 6.2 g (0.087 mol) of chlorine was dosed for 2 hours and under cooling, after which the mixture was again stirred for 5 hours at 23° C. The suspension was filtered and the crystals obtained washed with 30 ml of ethylbenzene. After drying under vacuum 14.65 g of a white crystalline substance was obtained.

The content was determined potentiographically as in Example I and amounted to 99.6% D-(-)-phenylglycine chloride hydrochloride and 0.4% D-(-)-phenylglycine hydrochloride.

I claim:

1. A process for the preparation of D-(-)-phenylglycine chloride hydrochloride, which comprises; chlorinating D-(-)-phenylglycine hydrochloride in a non-chlorinated solvent in the presence of a chlorination reaction promoting medium.

2. A process according to claim 1, wherein the chlorination is carried out through the addition of PCl$_5$.

3. A process according to claim 2, wherein the PCl$_5$ is prepared in situ from PCl$_3$ and Cl$_2$ gas.

4. A process according to claims 1–3, wherein the non-chlorinated solvent is selected from cyclohexane, cumene, ethyl benzene, heptane, mesitilene, pentane, toluene, xylene, or a mixture thereof.

5. A process according to claim 4, wherein the solvent is p-xylene.

6. A process according to claim 1, wherein the reaction promoting medium is selected from the group consisting of an oxychloride and an acylchloride.

7. A process according to claim 6, wherein the oxychloride is phosphorus oxychloride, thionyl chloride, sulfuryl chloride or vanadyl chloride.

8. A process according to claim 6, wherein the acylchloride is acetyl chloride, propionyl chloride or benzoyl chloride.

9. A process according to claim 1 carried out at a temperature within the range of 10° to 40° C.

10. A process according to claim 1 wherein the D-(-)-phenylglycine hydrochloride is prepared by the reaction of D-(-)phenylglycine and hydrochloric acid gas in-situ in the nonchlorinated solvent.

11. A process for the preparation of D-C(-)phenylglycine chloride hydrochloride, which comprises; suspending 5–30% by weight of D-(-)-phenylglycine hydrochloride in a non-chlorinated, biologically degradable solvent at a temperature of from 10° C. to 40° C.;

adding 5–45% by weight of a chlorination reaction promoting medium to the suspension;

chlorinating the suspension with the medium with stirring for 2 to 15 hours at a temperature of 10° C. to 40° C.;

separating the crystalline D-(-)-phenylglycine chloride hydrochloride; and recovering the chlorination reaction promotion medium for subsequent use in the process of preparing D-(-)-phenylglycine chloride hydrochloride.

12. A process according to claim 11 wherein the weight proportion of hydrochloride is within the range of 7 to 12 percent.

13. A process according to claim 11 wherein the weight proportion of medium is within the range of 20–25%.

14. A process according to claim 11 where chlorination is carried out at a temperature of 20°–25° C. for 5 to 10 hours.

15. A process according to claim 11 wherein the chlorination reaction promoting medium is selected from the group consisting of an oxychloride and an acylchloride.

16. A process according to claim 15 wherein the chlorination reaction promoting medium selected is an oxychloride selected from the group consisting of phosphorous oxychloride; thionyl chloride, sulfuryl chloride and vanadyl chloride.

17. A process according to claim 15 wherein the chlorination reaction promoting medium selected is an acylchloride selected from the group consisting of acetyl chloride; propionyl chloride and benzoyl chloride.

* * * * *